United States Patent [19]
Reinert

[11] Patent Number: 5,632,730
[45] Date of Patent: May 27, 1997

[54] FLUID INJECTOR

[76] Inventor: Charles B. Reinert, 701 E. Division St., Alton, Iowa 51003

[21] Appl. No.: 543,379

[22] Filed: Oct. 16, 1995

[51] Int. Cl.$^6$ ............................................. A61M 5/20
[52] U.S. Cl. ................................ 604/137; 604/131
[58] Field of Search ........................ 604/131, 134, 604/135, 136, 137; 128/749, 753, 754

[56] References Cited

U.S. PATENT DOCUMENTS

| | | | |
|---|---|---|---|
| 530,187 | 12/1894 | Laskey . | |
| 3,016,897 | 1/1962 | Kendrick . | |
| 3,114,370 | 12/1963 | Kayler | 604/137 |
| 3,430,626 | 3/1969 | Bergman | 604/137 |
| 3,494,358 | 2/1970 | Fehus | 604/137 |
| 3,809,083 | 5/1974 | Westergaard | 604/137 |
| 4,403,989 | 9/1983 | Christensen et al. . | |
| 4,487,602 | 12/1984 | Christensen et al. . | |
| 4,642,099 | 2/1987 | Phillips et al. . | |
| 4,676,781 | 6/1987 | Phillips et al. . | |
| 4,699,154 | 10/1987 | Lindgren | 128/754 |
| 4,717,383 | 1/1988 | Phillips et al. . | |
| 5,141,496 | 8/1992 | Dalto et al. . | |

OTHER PUBLICATIONS

Copy–1 page document entitled "Syringes and Hypodermic Needles II" from Jorgensen Laboratories, Inc.–1994 Product Catalog (p. 9).

Copy–1 page document entitled "II Syringes and Hypodermic Needles" from Jorgensen Laboratories, Inc.–1994 Product Catalog.

Copy–1 page document entitled "Hypodermic Syringes & Needles" from Ideal Instruments 1993 Product Catalog (p. 3).

*Primary Examiner*—Sam Rimell
*Assistant Examiner*—Luke Yeh
*Attorney, Agent, or Firm*—Henderson & Sturm

[57] ABSTRACT

An injector to deliver a variable dose into a living creature, such as an animal, the injector having a mounting element with an elongated, straight handle to be gripped by the user, a cylinder fixed to the mounting element, a piston movably associated within the cylinder to define a variable volume working space, a tube connected to the piston and fluidly connected to the space through the piston, a needle fluidly communicating with the space, check valves controlling the flow of fluid, a pad associated with the needle and the mounting element, the pad having a face with an oblique angle of engagement with the animal, the piston movable to a cocked position by the tube where it is retained until automatically released upon said pad contacting the animal and being moved toward the body, and thereby permitting the needle to be inserted into the animal, the pad engaging a latch binding the tube in the cocked position for releasing the tube and piston for passage of fluid from the space through the needle, a pawl for holding the latch in a non-tube binding position until a full dose of fluid has been ejected through the needle and further ensuring full needle penetration, and an element connected to the tube for engagement with the handle for varying the amount of the working space.

16 Claims, 5 Drawing Sheets

5,632,730

FLUID INJECTOR

TECHNICAL FIELD

This invention relates to injectors or syringes for injecting a predetermined but variable dose of a fluid through a needle by forcing the needle through and below the skin of particularly, but not exclusively, an animal.

BACKGROUND ART

Most contemporary animal injectors have a plurality of problems; such as length of time for each individual use; bending of needles due to improper design of the injector, such bending causing abscesses to the skin; inconsistency of dosage due to attempted quick use; and inability to maneuver the injector close enough particularly to a moving animal.

All of these and other problems are exacerbated when the injector is being used by, for example, a veterinarian inoculating literally hundreds of animals at a time. It is to a solution of such problems that this injector is directed.

DISCLOSURE OF THE INVENTION

The present invention provides an injector of an elongated, slim design, having a handle whereby the operator can insert the injector through or between any known cages or other animal holding structures for certain, full contact with the skin of the animal. It provides further a pad with an oblique facing surface adapted for gripping and holding the animal skin while simultaneously stretching the skin immediately prior to insertion of the needle.

The injector also has an elongated fluid delivery tube associated with the handle, and connected to a piston within the fluid cylinder for delivering fluid to the variably working volume space therein, and which tube and piston are movable to a cocked position and held therein by a latch which binds, in one position, the tube against movement; and with the pad movable toward the latch upon engagement of the pad with the animal skin and adapted to engage and move the latch out of its tube-binding position such that the tube and piston are free to force fluid out of the space and through the needle.

To ensure that the full, predetermined dose of fluid is ejected, a pawl is provided to hold the latch out of its tube-binding position until the piston moves the full preset length of the space, whereupon the latch is released to assume its normal, tube-binding position. Even when cocked, though the tube is moved in one direction relative to the latch, the latch prevents the tube from moving in the opposite direction.

The injector provides, thus, that a shot or injection of desired dosage cannot be tripped or delivered until the proper needle depth is obtained.

The handle of the injector is elongated, slim and of a "straight on" design as opposed to a right angle handle which translates to less needle bending forces during the injection process and the reaction of the animal from a needle stick. The length of the handle also keeps the operator a safe distance from the animal being inoculated. An infinitely variable dosage is also provided by a simple nut threaded onto the rear end of a fluid delivery tube and operable in conjunction with the handle.

At the forward end of the handle, a movable pad unit is provided, with a foot having a face with a variable angle of engagement with the animal, and designed such that upon engagement, the skin of the animal is stretched before needle penetration, thus diffusing pressure away from the needle. Further, the pad unit rebounds the injector quickly away from the animal after injection. The pad unit also encloses the needle prior to injection for protection against accidents to both persons and animals.

BEST MODE FOR CARRYING OUT THE INVENTION

Figure 1:
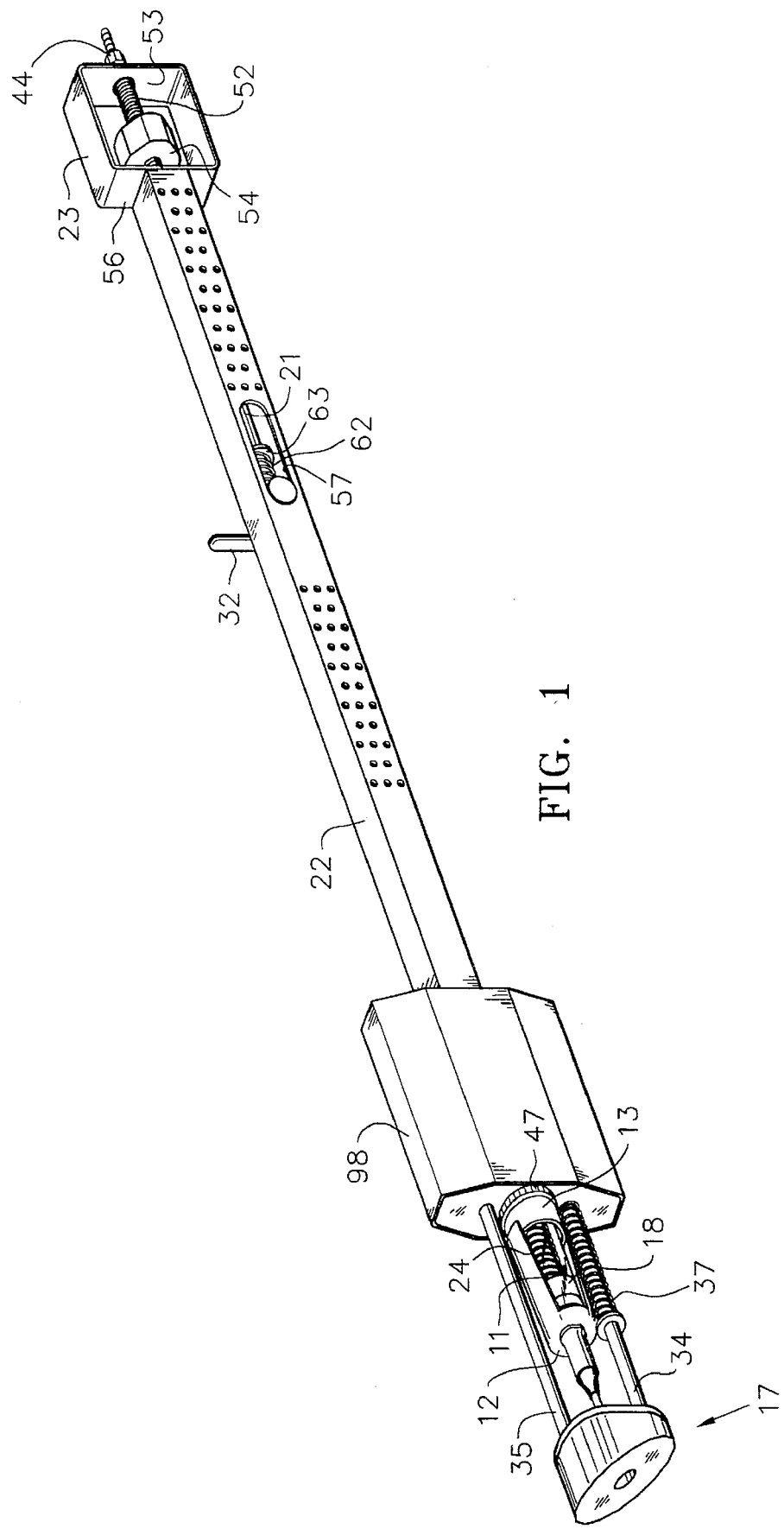
FIG. 1 is a perspective view of the fluid injection device of the present invention.
Figure 3:
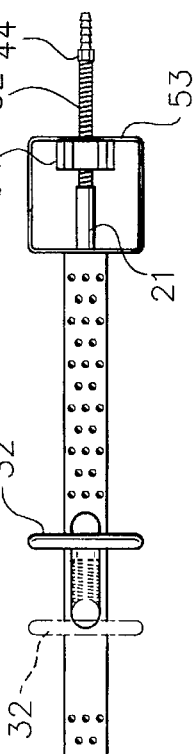
FIG. 3 is a view similar to FIG. 2, but with the tube and piston moved to a cocked position.
Figure 3:
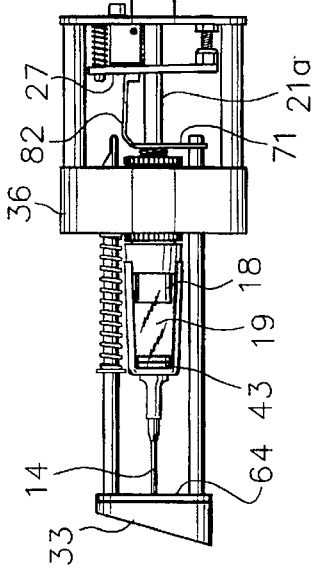
Figure 4:
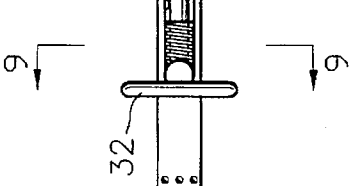
FIG. 4 is a view showing the fluid injector with an animal contact pad shown by full lines in a fully retracted position and by dash lines in a position similar to FIGS. 1 and 2.
Figure 4:
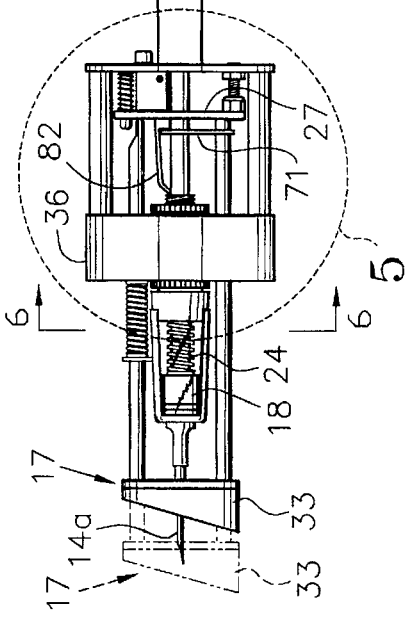

Referring to FIG. 1, the fluid injector of this invention, designed to deliver a required dosage of fluid, such as a serum, into an animal or other living creature, has generally: a hollow cylinder (11) having a forward end (12) and a rear end (13); a needle (14) fixed to the forward end (12) and in fluid communication therewith; a mounting element (16) (FIG. 2) secured to the rear end (13); an animal contact shroud or pad unit (17) connected to the mounting element (16) for relative movement longitudinally of the cylinder (11), the needle (14) extended through the pad unit (17) (see FIG. 4); a piston (18) mounted for longitudinal movement within the cylinder (11) to define a variable volume working space (19) (FIG. 3) therein.

Figure 6:
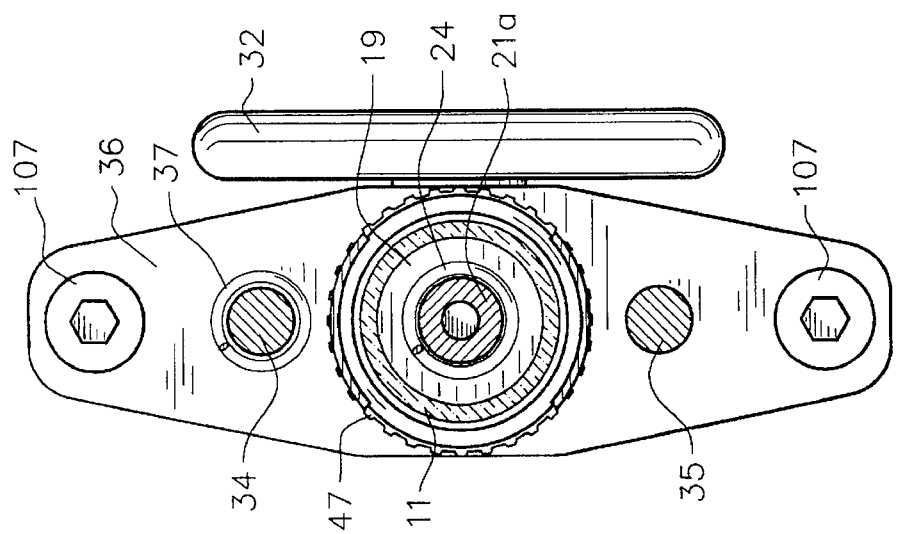
FIG. 6 is a further enlarged sectional view as taken along the line 6—6 in FIG. 4.
Figure 10:
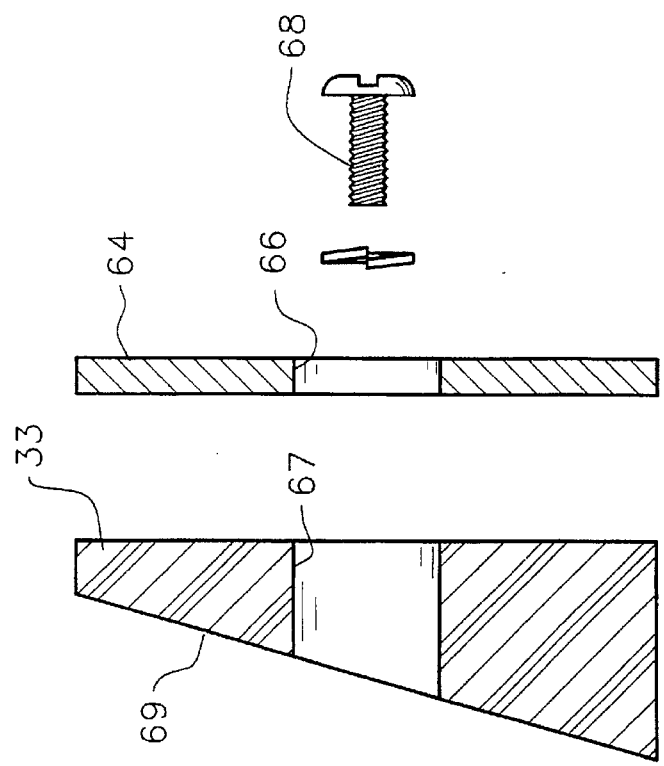
FIG. 10 is an exploded view, in section, of the animal contact pad unit.
Figure 9:
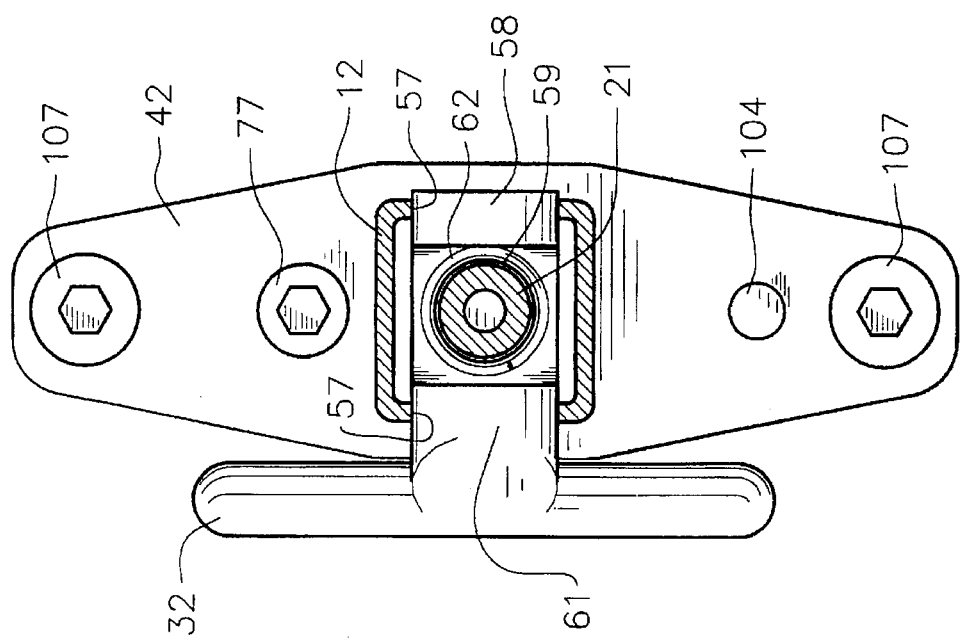
FIG. 9 is a sectional view as taken along the line 9—9 in FIG. 4.

The fluid injector has further an elongated hollow delivery tube (21) extended through the mounting element (16) and into a fluid connection at its from end (21a) (FIG. 6) with the piston (18) for delivering a supply of serum through the piston (18) for entry into the working space (19) of the cylinder (11). The delivery tube (21) and the piston (18) move together such that the piston (18) moves within the cylinder (11) between a rest position (see FIG. 2) defining a minimum volume of space (19), and a cocked position (see FIG. 3) at the rear of the cylinder (11) defining a maximum volume of working space (19) for the serum. As will be seen hereinafter, the working space can be readily varied between the maximum and minimum.

Figure 5:
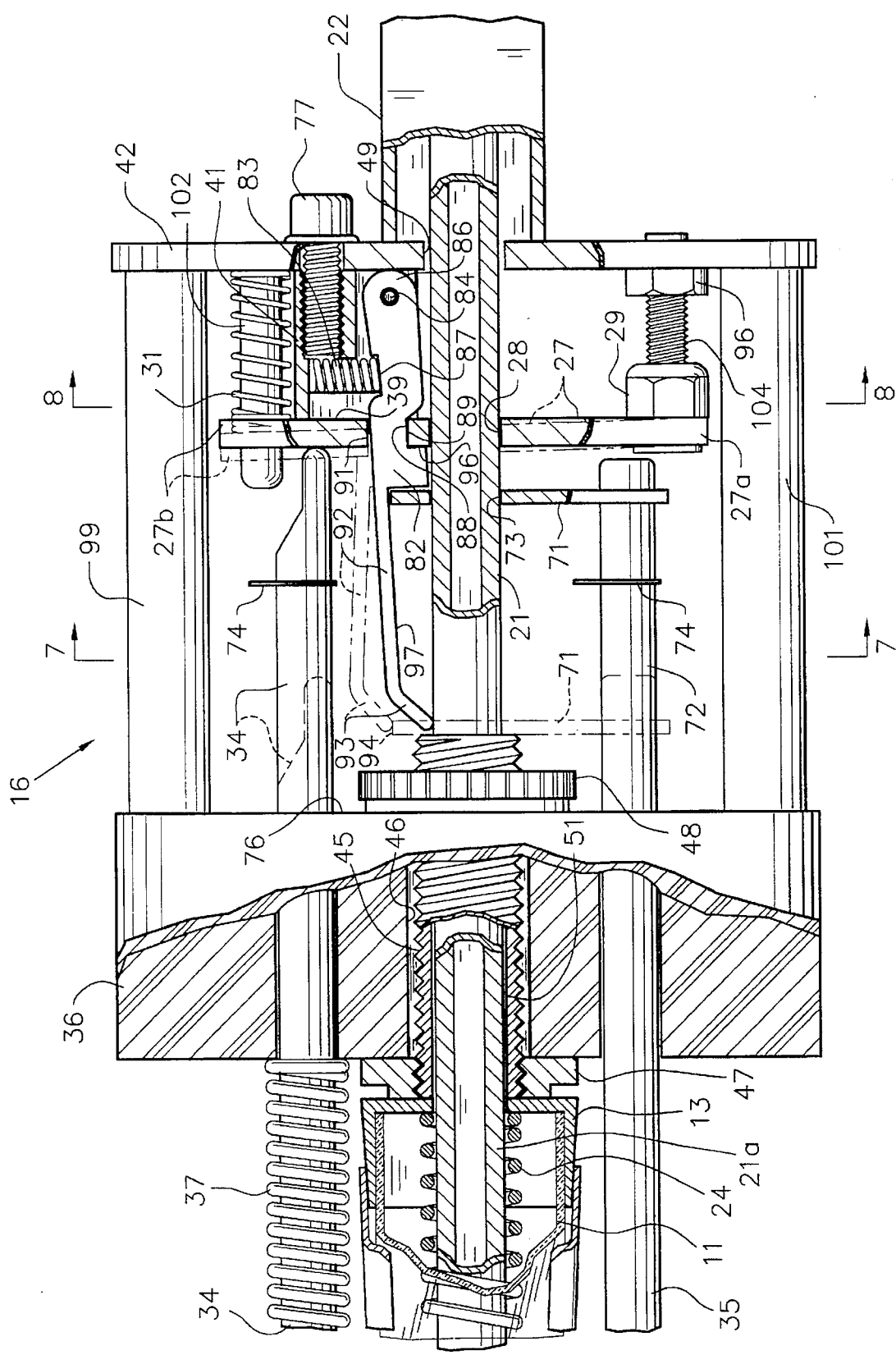
FIG. 5 is an enlarged detail view of FIG. 4 as shown in the dash circle thereof, with certain parts in different positions by the use of full and dash lines, and with other parts broken away for clarity of illustration.

The delivery tube (21) is disposed within an elongated handle (22), the rear end (21b) of the tube (21) extended rearwardly of the handle (22) and through a square, open plate (23); a first spring (24) being provided surrounding the delivery tube from end (21a) and disposed between the piston (18) and the rear (13) of the cylinder (11) for biasing the piston (18) and delivery tube (21) as a unit from the cocked position toward the rest position; and the fluid injector comprising further a flat, latch (27) (FIGS. 4 and 5) as part of a latching device (25) through which the delivery tube (21) loosely extends, the latch (27) movable between a first position retaining the delivery tube (21) in its cocked position-see FIG. 5 in the dash position of the latch (27), and a second position releasing the delivery tube (21) to the bias of the first spring (24)-see FIG. 5 of the latch (27) in its full line position.

The latch (27) has an opening (28) (FIG. 5) formed therein slightly larger than the outer diameter of the delivery tube (21) whereby the latch (27), held against axial movement at its base (27a) by a nut (29), may move pivotally about its base (27a) sufficiently from a position normal to the delivery tube (21), whereby the delivery tube (21) and piston (18) can move forwardly relative to the cylinder (11), to a non-normal position (dotted line position of latch (27) in Fig. 5)) such that the latch (27) frictionally binds the tube (21) from such forward movement. A second spring (31) (FIG. 5) is provided for biasing the top (27b) of the latch (27) forward for normally maintaining the latch (27) in its tube-binding position.

To cock the piston (18), a lever (32) (FIG. 2) secured to the delivery tube (21) is manually pulled rearwardly of the handle (22) a predetermined distance described more in detail hereinafter, pulling the piston (18) rearwardly against the forward bias of the first spring (24). The rearward movement of the delivery tube (21) frictionally causes the latch (27) to move from its non-normal (dash line) position (FIG. 5) toward its normal (full line) position (FIG. 5) such that the delivery tube (21) moves freely rearwardly through the latch opening (28), pulling the piston (18) rearwardly from its rest position (FIG. 2) to its cocked position (FIG. 3) within the cylinder (11), and with serum filling the working space (19) as detailed hereinafter.

To release the piston (18) and delivery tube (21) from their cocked position, the pad unit (17) includes an animal contact pad (33) with a pair of upper and lower rods (34), (35), respectively, disposed in a parallel relationship and longitudinally movable through a front, plastic block (36) (FIGS. 4 and 6) of the mounting element (16). Upon engagement of the pad (33) with an animal to be injected, by the operator holding the handle (22) and forcing it toward the animal contact area, the pad (33) and rods (34), (35) are free to move rearwardly of the block (36) against the bias of a spring (37) embracing the upper rod (34) and disposed between the block (36) and a clip (38) on the rod (34). Rearward movement of the rods (34), (35) stops upon engagement of the upper rod (34) with the latch (27), and pivotal movement - due to the rod (34), of the latch (27) from its tube-binding position (FIG. 5) to its tube releasing position, the latch top (27b) engaging a front edge (39) (FIG. 5) of a housing (41) secured to a plate (42) at the rear of the mounting element (16). As stated hereinbefore, upon the latch (27) being moved to its position (full lines, FIG. 5) normal to the delivery tube (21), the tube (21) and piston (18) are free to move forwardly under the bias of the first spring (24) thus ejecting the serum from the cylinder (11) through the needle (14) and into the animal.

More particularly, the front end (12) of the cylinder (11) includes a one-way check valve (43) (FIG. 3) and which valve works in conjunction with another one-way check valve (not shown) mounted within and as a part of the piston (18). Upon retracted movement of the delivery tube (21) to its cocked position, the piston (18) check valve permits serum to flow forwardly through the tube (21), from a source of serum normally connected to the rear end (44) (FIG. 4) of the delivery tube (21), and into the cylinder working space (19) (FIG. 3) due to suction pressure, with the other check valve (43) closed. Then upon forward movement of the piston (18) within the cylinder (11) the piston check valve closes and the cylinder check valve (43) opens to permit the serum within the working space (19) to be ejected therefrom. The rear end (13) of the cylinder (11) is formed as a cavity to receive the first spring (24) in a compressed condition.

Beyond the cylinder rear end (13) extends an externally threaded projection (45) (FIG. 5) which extends through a bore (46) formed through the center of the block (36), the projection (45) and thus the cylinder (11) being secured in a fixed position to the block (36) by a pair of internally threaded nuts (47), (48) threaded onto the projection (45) and up against opposite sides of the block (36). The delivery tube (21) extends forwardly through the handle (22) (FIG. 5), through an opening (49) in the rear plate (42) of the mounting element (16), through a bore (51) formed in the projection (45), and also through the cylinder rear end (13) and into the cylinder (11), it being remembered the delivery tube (21) is longitudinally movable relative to these elements. An externally threaded portion (52) (FIG. 3) is formed at the rear of the delivery tube (21) for passage through the legs (53), (56) of the plate (23).

To vary the dosage of serum an infinite amount, a hand rotated nut (54) (FIG. 4) is threaded onto the delivery tube rear portion (52) between the legs (56), (53) of the plate (23). The cylinder (11) is of a size to hold up to 5 millimeters of serum for example, and has graduated indicia thereon (not shown) for that purpose, such that by threadably adjusting the nut (54) on the delivery tube (52), the cocked position of the piston (18) within the cylinder (11) is determined by the amount of retraction or rearward movement of the delivery tube (21) relative to the cylinder (11) permitted, as determined by the nut (54) engaging the plate rear leg (53) (FIG. 3).

To aid the cocking of the delivery tube (21), the handle (22) has an elongated slot (57) (FIGS. 4, 9) formed therein, through which the T-shape lever (32) extends, the lever base (58) having a passage (59) (FIG. 9) movably receiving the delivery tube (21), and with a neck portion (61) of the lever (32) protruding through the slot (57). A spring (62) surrounds the delivery tube (21) between the lever base (58) and a clip (63) secured to the tube (21), such that the delivery tube (21) and piston (18) are cocked by operator finger manipulation of the lever (32) rearwardly of the handle (22) against the bias of the spring (24), the delivery tube (21) moving rearwardly until the dose adjustment nut (54) engages the plate rear leg (53). Spring (62) maintains the cocking handle (22) at the forward end of the slot (57) when the handle (22) is not being used. The length of the slot (57) is sized to accommodate the maximum amount of dosage as determined by the position of the nut (54), and subsequent to the cocking action, the spring (62) acts to return the lever (32) to its original position (FIG. 3).

The pad unit (17) includes further a plate (64) (FIG. 10) and the pad (33), both having appropriate central openings (66), (67), respectively, for receiving the needle (14), and connected by one or more screws (68). The pad (33) has a face (69) extended at an oblique angle to the longitudinal axis of the needle (14), and with the face (69) having a non-skid surface formed thereon, as desirable for better gripping action of the animal skin. The face opening (67) of the pad (33) is of a size sufficient to effect-upon engagement with the animal skin, a stretching of the animal skin for enhanced needle insertion. The pad (33) completely surrounds the forward tip end (14a) (see FIGS. 3 and 4) of the needle (14) and contains the tip end (14a) when the pad unit (17) is at a rest position. Optionally, the angle of the pad face (69) may be varied, and the pad (33) may be removed, leaving the plate (64), the face of that being of a non-skid surface, if desirable.

The lower rod (35) of the pad unit (17) has a lift plate (71) (FIG. 5) secured at its rear end (72) with an opening (73) formed therein through which the delivery tube (21) movably extends. Both rods (34), (35) have external retaining rings (74) secured thereto (FIG. 5) for limiting the forward movement of the pad unit (17) relative to the mounting element (16), the clips (74) engageable with the rear face (76) of the block (36).

Figure 8:
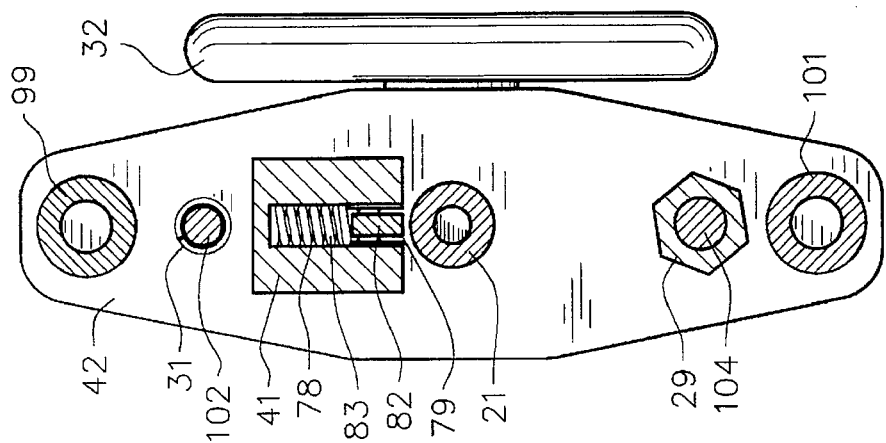
FIGS. 7 and 8 are further enlarged sectional views as taken along the lines 7—7 and 8—8, respectively, in FIG. 5.
Figure 7:
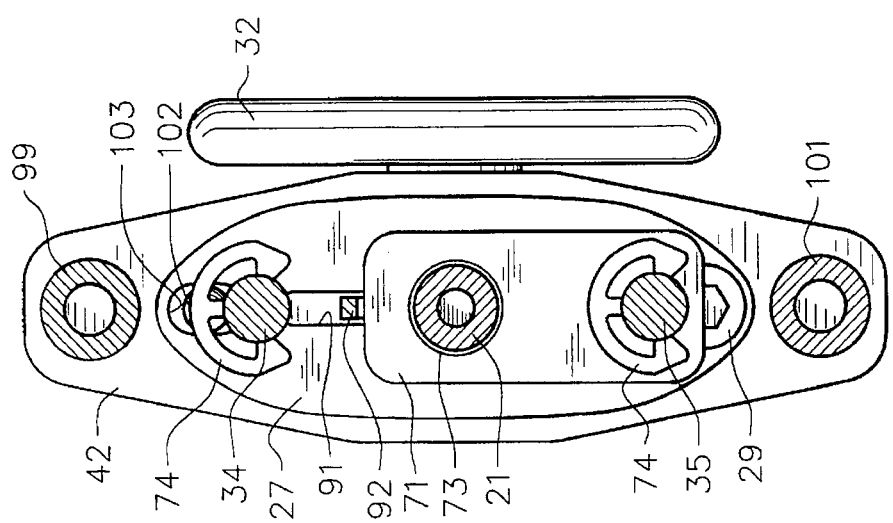

The latching device (25) includes further the housing (41) (FIGS. 5 and 8) being secured to the rear plate (42) by a screw (77) and with a central passage (78) (FIG. 8) formed therein, open at the bottom (79) (FIG. 8) and front (81) (FIG. 2) of the housing (41) for holding a pawl (82) and a spring (83) for the pawl (82). As best seen in FIG. 5, the pawl (82) is long and thin, pivoted at (84) at its rear (86) to the housing (41), having a notch (87) on a top edge for receiving the spring (83), having a cutout (88) on a lower edge for resting on the lower edge (89) of a vertical slot (91) (FIG. 7) formed in the latch (27) above the opening (28) for the delivery tube (21), and with the front end of the latch formed as a finger (92) the outer tip (93) of which is curved downwardly relative to the remainder of the finger (92). One manner of holding the nut (29) snugly against the latch base (27a) (FIG. 5), but such that the latch (27) may pivot, is the provision of a shaft (104) (FIG. 8) secured in turn by a hex nut (96) to the rear plate (42). The second spring (31) (FIGS. 5 and 7) is mounted on a shaft (102) secured to the plate (42) and extended toward and through an enlarged slot (103) formed in the latch (27), whereby the upper end (27b) of the latch (27) is free for the required arcuate pivotal movement about its base (27a).

Figure 2:
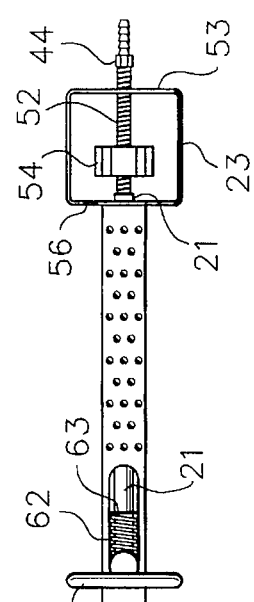
FIG. 2 is a side elevational view of the fluid injector of FIG. 1, with a shield removed and showing the injector in an inoperative position.
Figure 2:
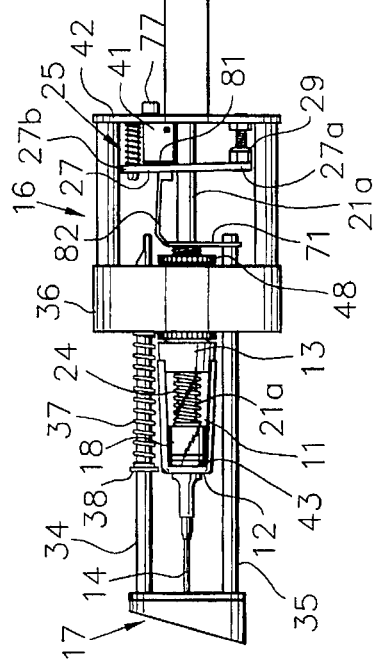

Referring to FIGS. 1 and 2, the front block (36) and rear plate (42) of the mounting element (16), including all of the elements shown therebetween in FIG. 5 are enclosed by a hollow shield (98). The shield (98) may have a frictional fit with the block (36) and plate (42), or may be fastened thereto as desired. Further, the block (36) and plate (42) are interconnected by a pair of spacer tubes (99), (101) (FIG. 5) and appropriate fasteners (102).

In operation, it was described hereinbefore that the amount of dosage was determined by the position of the dose adjustment nut, and that the dosage within the variable volume working space (19) was delivered due to the upper rod (34) of the pad unit (17) engaging and moving the latch (27) from its delivery tube-engaging or binding position to its delivery tube-releasing position. Assuming that the handle (22) is held with sufficient force to hold the pad unit (17) against the animal to thereby hold the pad unit (17) in its retracted position a sufficient time to permit the first spring (24) within the cylinder (11) to effect a full forward movement of the piston (18) and delivery tube (21) to their full forward or rest position, the latch (27) being held in its position normal to the delivery tube (21), a full dosage is injected.

It can readily be appreciated that should the handle (22) be pulled away prematurely, or should the animal itself move away prematurely, leaving the pad unit (17) to spring back toward its forward, rest position, as soon as the upper rod (34) disengages from the latch top end (27b), the latch spring (31) will immediately force the latch (27) back into its normal tube-binding position. Thus, the delivery tube (21) and the piston (18) could be stopped and held in a position intermediate their cocked and rest positions. Only a partial dosage would then be discharged from the cylinder space (19) through the needle (14).

To ensure a full dosage is ejected, the pawl (82) and lift plate (71) coact with the latch (27). It will be noted from FIGS. 1 and 5 that when the piston (18) and delivery tube (21) are in their forward rest position, the finger tip (93) of the pawl (82) rests upon the upper end (94) of the lift plate (71), thus raising the pawl bottom cutout (88), and the shoulder (96) formed thereby, above the lower edge (89) of the latch slot (91). In this position of the pawl (82), the delivery tube (21) is free to move forwardly toward its rest position or rearwardly toward its cocked position. Note further that the spring (83) is biasing the pawl (82) from raised position just described - see dash lines in FIG. 5, toward a lowered position.

Even in the cocked position of the piston (18) and delivery tube (21) (FIGS. 3 and 5), the pawl (82) remains in its raised position. However, upon rearward movement of the pad unit (17), as soon as the lift plate (71) moves rearwardly see dash position of FIG. 5, and from under the fingertip (93), the pawl (82) will immediately pivot downwardly due to the spring (83) to the full line position of FIG. 5, such that upon the upper rod (34) engaging and moving the latch (27) to its full vertical or normal position, the pawl cutout (88) and shoulder (96) will engage and lock the latch (27) in the tube-releasing position. As the amount of longitudinal movement of the lift plate (71) (FIG. 5) is the equal of like longitudinal movement of the piston (18) for a full dose discharge, even though the latch (27) has been released by the pad unit upper rod (34), the latch (27) is retained in its non-tube binding position until a full dosage has been ejected and the lift plate (71) is returned, sliding along the underside (97) of the finger (92) without raising the pawl (82) sufficiently to release the latch (27), to its full forward position, as shown by dash lines in FIG. 5.

In that position, the upper end (94) of the lift plate (71) again engages and pivotally raises or lifts the pawl (82) within the slot (91) and against the bias of the spring (83) sufficiently for the latch slot lower edge (89) (FIG. 5) to be clear of the pawl (82), whereby the spring (31) is then effective to move the latch (27) to the delivery tube-binding position. Ejection of a full dosage is thereby ensured. It will thus be seen that all of the objectives of the invention have been fulfilled.

I claim:

1. A fluid injector to deliver a required dose into an animal or other living creature, comprising:

means forming a handle;

means forming a fluid delivery tube connected to said handle means, said delivery tube movable relative to said handle means;

means forming a cylinder fluidly connected to said fluid delivery tube;

a piston movably disposed within said cylinder and fluidly connected to said delivery tube, said piston forming a volume working space within said cylinder, said piston movable with said delivery tube;

valve means interposed in said cylinder and said piston for controlling the flow of fluid into and out of said cylinder space;

a needle fluidly connected to said cylinder for transmitting fluid from said cylinder space;

said piston and said delivery tube movable between a cocked position wherein fluid is drawn into said working space, and a rest position; and latch means connected to said delivery tube and movable between a position retaining said delivery tube against movement out of said cocked position, and a position releasing said delivery tube for movement to said rest position, wherein said piston is moved within said cylinder to force fluid out of said working space and through said needle for ejection, therefrom.

2. The fluid injector of claim 1, and further wherein said latch means includes a latch through which said delivery tube extends for movement in opposite directions, said latch movable between a first position relative to said delivery tube wherein said delivery tube is free to move, and a second position wherein said latch frictionally engages said delivery tube and prevents movement of said delivery tube in one said direction.

3. The fluid injector of claim 2, and further wherein in said first position said latch is disposed normal to said delivery tube, and in said second position said latch is disposed oblique to said delivery tube.

4. The fluid injector of claim 1, and further wherein means forming a pad unit for engaging an animal is mounted on said handle, said pad unit means movable longitudinally of said cylinder between a first position forwardly of said needle to a second position engaging and moving said latch means to its said delivery tube releasing position.

5. The fluid injector of claim 4, and further wherein means forming a pawl unit is provided for retaining said latch means in its said delivery tube releasing position until said piston is moved to its said rest position.

6. The fluid injector of claim 1, and further wherein means for varying the amount of fluid ejected from said cylinder working space is mounted on said delivery tube for movement longitudinally thereof, and for engagement with said handle means to limit the amount of movement of said piston within said cylinder.

7. A fluid injector to deliver a required dose into an animal or other living creature, comprising:

a hollow cylinder having a forward end and a rear end;

a needle fixed to said cylinder at said forward end and fluidly connected thereto;

a mounting element secured to the rear of said cylinder;

an animal contact pad connected to said mounting element for movement longitudinally of said cylinder, said needle extendable through said pad;

a piston mounted within and cooperating with said cylinder to define a variable volume working space therein;

an elongated hollow delivery tube extended through said mounting element and into a fluid connection with said piston for delivering a supply of fluid through said piston for entry into said cylinder, said piston being longitudinally movable within said cylinder between a rest position defining a minimum volume for said space and a rear cocked position defining a maximum volume for said space, said delivery tube being movable with said piston;

an elongated handle extended alongside said delivery tube;

a first spring engaging said piston for biasing said piston from said cocked position toward said rest position;

a latch movable between a first position retaining said delivery tube in said cocked position and a second position releasing said tube to the bias of said first spring;

a second spring for biasing said latch into said first position; and a rod unit connected to said pad and extended through said mounting element and operable upon engagement of said pad with an animal to be injected to move longitudinally of said cylinder to a retracted position to move said latch against the bias of said second spring into said second position for releasing said delivery tube from said cocked position for moving said piston to force fluid from within said cylinder and through said needle for discharge therefrom.

8. The fluid injector of claim 7, and further wherein said contact pad has a facing surface for engagement with the skin of the animal, said facing surface extended at an oblique angle to the longitudinal axis of said needle and having further an opening formed therein of a size sufficient to stretch the animal's skin for enhanced needle insertion.

9. The fluid injector of claim 8, and further wherein said facing surface has an anti-skid surface.

10. The fluid injector of claim 7, and further wherein a third spring is connected between said rod and said mounting element for biasing said pad from said retracted position to said forward position upon disengagement of said pad with an animal.

11. The fluid injector of claim 10, and further wherein said contact pad completely surrounds and contains the entire tip end of said needle within the contact pad at a forward position of said pad.

12. The fluid injector of claim 1, and further wherein said handle includes a plate at a rear end thereof, and said delivery tube has an externally threaded rear end longitudinally movable through said plate, and with a nut threadably mounted on said tube rear end for varying the distance of said tube-mounted nut from said plate, said nut engageable with said plate upon movement of said tube to said cocked position whereby to determine the movement of said piston within said cylinder and to vary the volume of working space therein.

13. The fluid injector of claim 7, and further wherein a lever is attached to said delivery tube and disposed externally of said handle for manual movement of said tube to said cocked position, and further wherein said lever extends normal to the longitudinal axis of said handle for manual engagement.

14. The fluid injector of claim 7, and further wherein said latch has opposed ends and an opening centrally thereof through which said delivery tube movably extends, one end of said latch being connected to said mounting element whereby said latch is pivotally movable about said one end between said first position disposed non-normal to said delivery tube whereby said latch binds said delivery tube against longitudinally movable from said cocked position to said rest position, and said second position disposed normal to said tube whereby said tube is free for longitudinal movement from said cocked position to said rest position.

15. The fluid injector of claim 14, and further wherein said second spring is disposed between said other end of said latch and said mounting element, and said rod unit is engageable with said other end of said latch for pivotally moving said latch into said first tube-binding position.

16. The fluid injector of claim 7, and further wherein a pawl is pivotally connected at one end to said mounting element for pivotal movement toward and away from said delivery tube, said pawl having a first position permitting said latch to assume its said first tube-binding position, and having a second position locking said latch in its second tube-releasing position.

* * * * *